United States Patent [19]

Eckberg

[11] Patent Number: 5,260,455
[45] Date of Patent: Nov. 9, 1993

[54] POLYEPOXYSILANES AND RADIATION-CURABLE POLYEPOXYSILICONE COMPOSITIONS

[75] Inventor: Richard P. Eckberg, Saratoga Springs, N.Y.

[73] Assignee: General Electric Company, Waterford, N.Y.

[21] Appl. No.: 910,463

[22] Filed: Jul. 8, 1992

[51] Int. Cl.$^5$ .................. C07F 7/08; C07D 303/02
[52] U.S. Cl. ................... 549/215; 522/25; 528/27
[58] Field of Search .......... 549/215; 522/25; 528/27

[56] References Cited

U.S. PATENT DOCUMENTS

| | | | |
|---|---|---|---|
| 2,730,532 | 1/1956 | Martin | 549/215 |
| 2,843,560 | 7/1958 | Mika | 549/215 X |
| 3,219,624 | 12/1965 | Cohen | 549/215 |
| 3,516,964 | 6/1970 | Patterson | 549/215 X |
| 4,082,726 | 4/1978 | Mine | 549/215 X |
| 4,208,503 | 6/1980 | Martin | 549/215 X |
| 4,313,988 | 2/1982 | Koshar et al. | 428/40 |
| 4,946,818 | 8/1990 | Lewis | 502/158 |
| 4,954,580 | 9/1990 | Zahir | 549/215 X |
| 4,977,198 | 12/1990 | Eckberg | 549/215 X |
| 4,987,203 | 1/1991 | Saho et al. | 528/27 |

OTHER PUBLICATIONS

E. P. Plueddemaun and G. Fanger, J. Amer. Chem. Soc., 81, 2632 (1959).
Eckberg et al., Radtech '90, North America Conference Proceedings, Chicago, pp. 358-370.

*Primary Examiner*—Paul F. Shaver

[57] ABSTRACT

Polyepoxy silane compositions resulting from the reaction of olefinepoxide and poly(H)silanes crosslink in the presence of a catalytic amount of an 'onium catalyst when exposed to UV light. In one embodiment, two moles of an olefin-containing epoxy monomer are reacted with a bis(H)-containing silane of general formula $R_2SiH_2$. Important to the success of this process is that $RhCl_3 \cdot xH_2O$ is capable of catalyzing the hydrosilation addition of 2 moles of olefin to $R_2SiH_2$. The resulting diepoxysilanes are reactive monomers which undergo photopolymerization when exposed to ultraviolet light in the presence of iodonium photocatalysts.

18 Claims, No Drawings

POLYEPOXYSILANES AND RADIATION-CURABLE POLYEPOXYSILICONE COMPOSITIONS

BACKGROUND OF THE INVENTION

The present invention relates to epoxysilanes and, in particular, to polyepoxysilanes curable in the presence of an 'onium salt catalyst when exposed to UV radiation.

Epoxysilicone polymers and epoxysiloxane monomers are readily prepared by platinum-catalyzed hydrosilation addition of olefin-epoxide monomers such as 4-vinyl cyclohexeneoxide (VCHO) and allylglycidyl ether (AGE) to the appropriate SiH-functional precursors, as described by E. P. Plueddemaun and G. Fanger, J. Amer. Chem. Soc., 81, 2632 (1959), and by R. J. Koshar et al., U.S. Pat. No. 4,313,988, among others. Further, it has been learned that certain rhodium hydrosilation catalysts are useful for synthesis of highly organofunctionalized epoxysilicone fluids and resins because they do not catalyze undesirable side reactions.

All of the references cited above teach the synthesis of epoxysilanes or epoxysiloxanes which are confined to mono-epoxy functionality attached to a silicon atom which in turn possess one or more Si—O bonds. Such materials can be represented as:

where $x \geq 1$ and E has the general formula

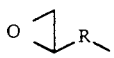

where R is an aryl, alkyl cycloalkyl group, ether, or other hydrocarbon having from 1 to about 20 carbon atoms. Exemplary epoxides include:

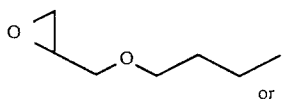

or

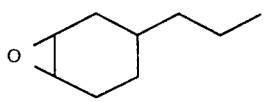

Platinum catalysts commonly used to process these materials are not effective for synthesis of polyepoxyalkylsilanes such as $E_x Si R_{4-x}$ where $x > 1$ and E is as defined above. Platinum catalysts commonly promote the addition of only one mole of olefin to an =SiH$_2$ or —SiH$_3$ species, which may account for the fact that polyepoxysilanes or polyepoxysilyl derivatives are not known.

SUMMARY OF THE INVENTION

The present invention is based upon the discovery that polyepoxysilane compositions resulting from the reaction of olefinepoxide and poly(H)silanes crosslink in the presence of a catalytic amount of 'onium catalyst when exposed to UV light. In one embodiment, synthesis of silahydrocarbons has been demonstrated, in particular $CH_3Si(C_{10}H_{21})(C_8H_{17})_2$, via stepwise addition of decene to MeHSiCl$_2$ followed by reduction of Me(C$_{10}$H$_{21}$)SiCl$_2$ to Me(C$_{10}$H$_{21}$)SiH$_2$, and finally addition of 2 moles of octene to the silane intermediate. Important to the success of this process is that RhCl$_3$·xH$_2$O is capable of catalyzing the hydrosilation addition of 2 moles of olefin to R$_2$SiH$_2$. Diepoxysilanes produced via analogous addition of 2 moles of olefin-epoxide to R$_2$SiH$_2$ are reactive monomers which undergo photopolymerization when exposed to ultraviolet light in the presence of 'onium photocatalysts.

In accordance with the invention, a polyepoxysilane having the general formula $E_xSiR_{4-x}$ is provided wherein x is $>1$ and each E is independently selected from the group of epoxides of the general formula:

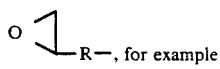

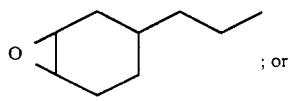

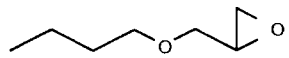

each R is independently selected from the group consisting of hydrogen and a hydrocarbon having from 1 to about 20 carbon atoms. Preferably E represents the radical:

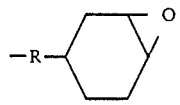

wherein R is an alkylene radical having from 1 to about 10 carbon atoms and more preferably an ethylene radical. The composition is produced from the hydrosilation reaction of epoxide monomers and a silane in the presence of a catalytic amount of a rhodium catalyst.

In another embodiment, radiation curable polyepoxysilyl-stopped siloxane systems have the formula:

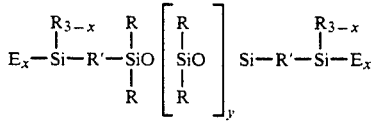

where $x = 2$ or 3,

R' and R are independently elected from hydrogen or hydrocarbons having from 1 to about 20 carbon atoms, and y is up to about 100; preferably about 25 to about 75.

These systems are radiation (i.e., UV or E-beam) curable in the presence of a catalytic amount of an 'onium salt.

DESCRIPTION OF THE INVENTION

The present invention is directed to the synthesis of polyepoxysilanes and the employment of such materials in the formulation of polyepoxysilicones.

According to the invention, epoxysilanes are produced which have the formula:

$$E_xSiR_{4-x}$$

where $x > 1$

E is independently selected from the group of epoxides of the general formula:

O for example:

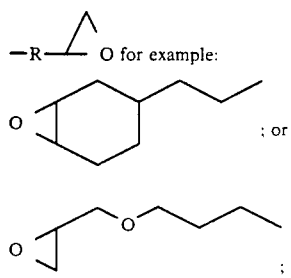

each R is independently selected from the group consisting of hydrogen and hydrocarbon radicals having from 1 to about 20 carbon atoms.

Preferably, E represents the radical

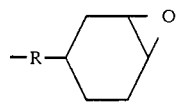

wherein in one embodiment, R is an alkene radical having from 1 to about 10 carbon atoms and is preferably an ethylene radical.

Polyepoxysilanes may be formed by a hydrosilation reaction of epoxide monomers such as olefin epoxides and a silane in the presence of a catalytic amount of a rhodium catalyst. The olefin epoxide includes monomers such as 4-vinylcyclohexeneoxide (VCHO) and allylglycidyl ether (AGE).

According to an embodiment of the present invention, the catalyst is $RhCl_3 \cdot xH_2O$ where x is from 2 to about 4.

The details as to the manufacture of the catalyst are set forth in U.S. Pat. No. 4,946,818 which is incorporated by reference herein.

In addition to the polyepoxysilanes, derivative compositions such as polyepoxysilyl-stopped siloxanes may be prepared. Such compositions have the general formula:

where x is 2 or 3,

R, R' are hydrocarbon radicals having from 1 to about 20 carbon atoms and y is up to about 100, preferably from about 25 to about 75. Preferably, R is the radical —$CH_3$. Preferably, R' is the radical —$CH_2CH_2$—. R" is a phenyl or a $C_4$ to $C_{20}$Alkyl, preferably hexyl.

In order to assist those skilled in the art, the following examples are presented by way of illustration but not limitation.

EXAMPLE I 46 g diphenylsilane (0.25 mole) + 108 g toluene were weighed into a 500 cc flask. 0.02 g of $RhCl_3 \cdot xH_2O$ were introduced to this solution as a methanol solution. This reaction mixture was brought to 114° C., then 70 g 4-vinylcyclohexeneoxide (VCHO) (0.56 mole) were added dropwise over a 65 minute period. Following the VCHO feed, the complete reaction mixture was maintained at 114° C. for 3 hours. FTIR analyses of the reaction mixture showed that a substantial loss of SiH had occurred, although the diphenylsilane was not totally consumed. 10 g (0.8 moles) additional VCHO plus a second charge of $RhCl_3 \cdot xH_2O$ equal to the first were then added, followed by a 2.5 hour hold at 114° C. (with agitation). At this time, no SiH was detected. 0.01 g $MeN(C_{18}H_{37})_2$ stabilizer was weighed into the product solution, which was then stripped of solvent and excess VCHO under vacuum at 134° C. for 1 hour. 96 g of extremely viscous, sticky product (90% of theory) were isolated. The residue flowed nicely at 70° C., behaving like a supercooled fluid at room temperature. While not completely characterized, the infrared spectrum of the product is consistent with the following proposed structure:

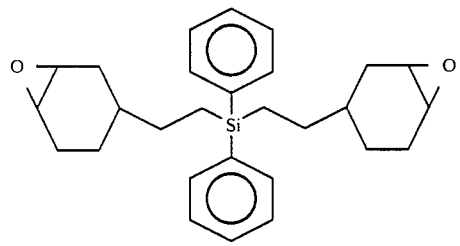

The refractive index of the product, $N_D^{25}$, = 1.5702 vs 1.580 for $Ph_2SiH_2$ starting material.

EXAMPLE II 46 g $Ph_2SiH_2$ (0.25 mole) were dispersed in a 500 cc flask with 108 g toluene + 0.03 g $RhCl_3 \cdot xH_2O$ as above, 64 g allylglycidylether (AGE) (0.56 moles) were added to the reaction mixture over a 30 minute period at 102° C. After the AGE was added, a latent exothermic reaction occurred which raised the reaction mixture to 120° C. for several minutes. A small amount of unreacted SiH was detected one hour after the exotherm had subsided, which was consumed by addition of fresh rhodium trichloride hydrate and 6 g additional allylglycidylether. Suspended particulate matter (probably rhodium metal) was filtered off, the product solution was then vacuum stripped at 150° C. (as above) to yield 82 g of fluid product, 228 cstk viscosity, $N_D^{25} = 1.5500$. The infrared spectrum of this material was consistent with the following proposed structure:

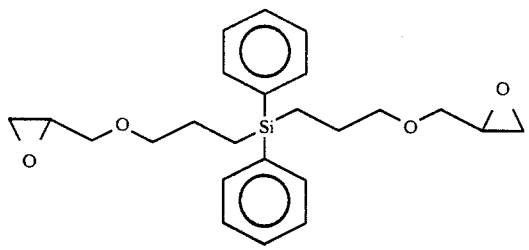

UV curability of these two materials was then assessed. Example I, Ph$_2$SiE$_2$, proved miscible with 1% (4-octyloxyphenyl) phenyl iodoniumhexafluoroantimonate (OPPI catalyst) at 75° C., but the catalyzed compound was too viscous to coat at <50° C. A 50 wt % solution of the catalyzed compound was then prepared in methylene chloride, and a 4 mil thick coating of the solution (~2 mils dry) was manually applied to polyethylene Kraft substrate. The coating was then exposed to focused UV light in an RPC Model QC1202 UV Processor to ascertain the minimum UV flux required to convert the liquid coating to a tack-free, migrationfree though-cured solid. Low-boiling methylene chlorine flashed off as the samples were passed under the hot UV lamps. The lower-viscosity Example II AGE derivative did not require a solvent vehicle to facilitate coating and UV cure analysis; Ph$_2$Si(GE)$_2$ proved miscible with 1 weight percent OPPI iodonium catalyst like its Ph$_2$Si E$_2$ analog. Results of the UV-cure assessment are tabulated below:

| 2 mil. R$_2$ Si E$_2$ = 1% OPPI Iodonium Catalyst on PEK | | |
|---|---|---|
| R | E | Minimum UV flux for Cure |
| Ph | (cyclohexene epoxide group) | 25 mJ/cm$^2$ |
| Ph | (glycidyl ether group) | 206 mJ/cm$^2$ |

Enhancement of physical properties of UV-cured films of epoxysilicone polymers requires that the crosslink density of cured films be reduced to the extent that about 50 or more—SiR$_2$O—groups be extant between reactive epoxy sites on the linear or precrosslinked epoxysilicone fluid discussed by Eckberg et al., Radtech '90 North America Conference Proceedings, Chicago, pp 358-370). Doing so drastically slows cure and/or polar iodonium catalyst solubility, however.

In accordance with the invention, it is believed that polyepoxysilyl-stopped linear dimethylsilicone systems, which can be regarded as derivatives of these polyepoxysilanes, combine good cured film properties with rapid UV-cure response and improved catalyst compatibility. Such polymers would cluster two or more polar epoxy groups at each end of the silicone molecule and have the formula:

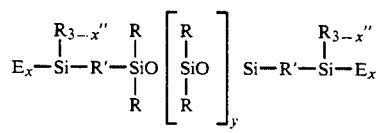

where X=2 or 3

R and R' are hydrocarbons having from 1 to about 20 carbon atoms and y is an integer up to about 100 and R" is as previously defined.

In a particular embodiment, the polymer may have the formula:

where x—2 or 3, y>50, and R is preferably CH$_3$.

It is theorized that synthesis of such unusual polymers could be carried out in this fashion:

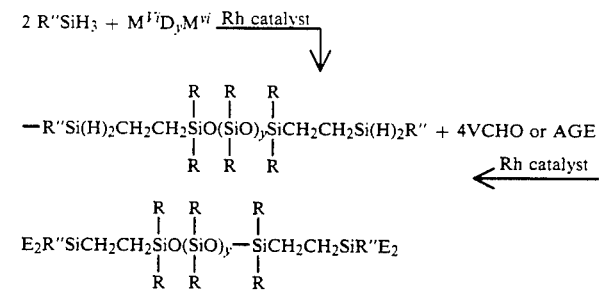

with R=alkyl or aromatic. In practice, R" would likely be limited to Ph or C$_4$ or higher alkyl.

Another possible route to produce polyepoxysilyl-stopped silicones is as follows:

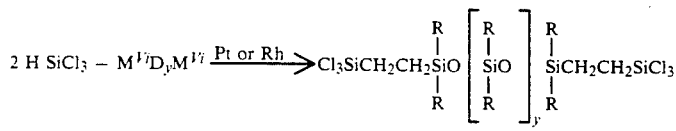

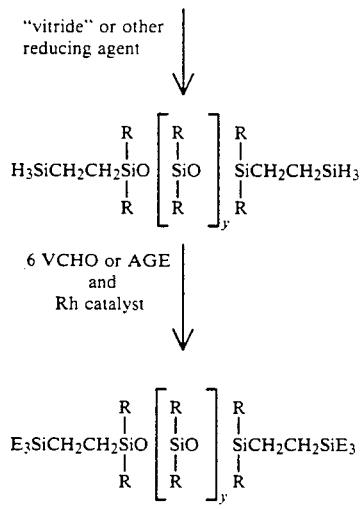

The following examples show various polyepoxy silanes which have been synthesized and characterized according to the methods described above.

EXAMPLE III

Monoepoxytriethylsilane was produced as a comparative material. 12 g triethylsilane (0.103 mole) were weighed into a 100 cc flask with 0.02 g of RhCl$_3$ hydrate as a dispersion in 0.5 cc ethanol. This mixture was treated with 30 g toluene, then brought to 113° C. and refluxed while 17 g 4-vinylcyclohexeneoxide (0.137 mol VCHO) were added dropwise. After the VCHO was added, the reaction mixture was held at reflux for 2 hours, at which point no SiH was detectable by IR. Toluene was distilled out of the product, leaving 20.2 g of a mobile fluid (81% yield). The infrared spectrum of the product was consistent with the structure Et$_3$Si(E), where Et is ethyl and E is —CH$_2$CH$_2$—cyclohexeneoxide. The refractive index n$_D^{25}$ was 1.4735 (vs. Et$_3$SiH n$_D$=1.4123).

EXAMPLE IV

Diepoxydiethylsilane 30 g diethylsilane (0.34 moles) were dispersed in 300 g toluene with 0.04 g RhCl$_3$ hydrate dispersed in 1 cc ethanol. This solution was brought to reflux (97° C., due to the 56° bp of the silane), then 120 g VCHO (0.97 moles, a 40% excess) were added dropwise over a 60 minute period. During this addition, the reflux temperature slowly increased to 110° C. A 4 hour hold at reflux caused loss of all reactive SiH per IR spectral analysis. Solvent was removed in vacuo at 80° C. to furnish 91 g of a viscous 3000 cps fluid product. The IR spectrum of this material was consistent with the proposed product but also indicated that some siloxanes also formed, probably from hydrolysis and reaction of ethanol with SiH. The refractive index of this product was 1.4885, compared to 1.392 for Et$_2$SiH$_2$.

EXAMPLE V

Diethyldiglycidylether Silane 22 g of diethylsilane (0.25 moles) were dispersed in 200 g toluene plus 0.04 g of rhodiumtrichloride hydrate (as a solution in 1 cc ethanol). The mixture was brought to 95° C. reflux as in Example IV above, when 70 g allylglycidylether were added (0.61 moles, 20% excess). Reflux temperature increased to 100° during the AGE addition. The batch was held at reflux overnight, which reduced the SiH content to a very small IR peak. Toluene and excess AGE were removed via strong nitrogen sweep at 120° for several hours. The product was a mobile fluid, 20 cstk viscosity, n$_D^{25}$=1.4670, with an infrared spectrum consistent with the proposed product plus a detectable level of siloxane formation.

EXAMPLE VI

Dihexyldiepoxysilane 60 g hexylsilane (C$_6$H$_{13}$)SiH$_3$ (0.52 moles) were dissolved in 600 g toluene with 0.06 g rhodiumtrichloride hydrate (in 1 cc ethanol). The solution was brought to 100° C., then 128 g VCHO (1.03 moles) were added over a one hour period, followed by a 3 hour hold at 105° C. The FTIR spectrum of the solution was compared with that of a blank consisting of all the mixture components without the rhodium catalyst, and it was found that the reaction mixture SiH absorption was ⅓ as great as that of the blank, indicating that an intermediate product (hexyl)SiH(E)$_2$ had been formed. 33 g of n-hexene (0.4 moles) were now slowly added to the refluxing solution over a fifty minute period, after which no SiH was detectable. Toluene was removed in a strong nitrogen sweep at 120° C. leaving 200 g of an 800 cps viscosity fluid product, N$_D^{25}$=1.4730, compared with N$_D^{25}$=1.4129 for the starting silane. As noted in the above examples, some siloxane impurity was present based on the product infrared spectrum.

EXAMPLE VII

Diphenylbis(5,6-epoxyhexyl)silane 27.6 g of diphenylsilane (0.15 mole) were dispersed in 100 g toluene with 0.02 g rhodiumtrichloride hydrate (as a solution in 0.5 cc ethanol) then the solution was brought to 100° C. when 32 g 1,2-epoxy-5-hexene (0.32 mole) were added dropwise. A two hour hold at 100°-110° followed, which consumed all SiH per IR analysis. Solvent was distilled off leaving 45 g residue as a mobile, 15 cstk viscosity fluid product, n$_D^{25}$=1.5532. Infrared analysis was consistent with the proposed structure, with evidence of siloxane by products also present.

These materials were all produced in similar fashion, namely, RhCl$_3$-catalyzed addition of two moles olefin epoxy monomer to various silane monomers including at least two Si-bonded H (except for the monofunctional triethylsilane example). Proposed structures for each example is set forth below in Table I:

TABLE I

| Example | Structure | Refractive Index |
|---|---|---|
| I | Ph$_2$SiE$_2$ | 1.5702 |
| II | Ph$_2$Si(GE)$_2$ | 1.5500 |
| III | Et$_3$SiE | 1.4735 |
| IV | Et$_2$SiE$_2$ | 1.4885 |
| V | Et$_2$Si(GE)$_2$ | 1.4670 |
| VI | (Hex)$_2$SiE$_2$ | 1.4730 |
| VII | Ph$_2$Si(HexE)$_2$ | 1.5532 | where:

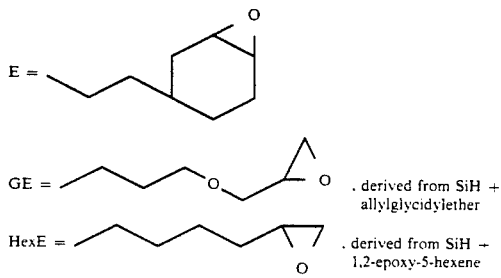

GE = ... derived from SiH + allylglycidylether

HexE = ... derived from SiH + 1,2-epoxy-5-hexene

A Si$^{29}$ NMR analysis was carried out on selected examples of the epoxy products and the silane precursors to better understand the nature of the reaction products. Spectra of these materials were consistent with formation of the proposed products plus significant amounts of hydrolysis products. The NMR spectra of the cyclohexylepoxy derivatives are complicated by the presence of endo- and exo-isomers of the cyclic epoxy group, leading to multiple peaks in the spectra. The results are summarized in the table below:

TABLE II

| Material | Si$^{29}$ Peaks | Relative Intensity |
|---|---|---|
| Ex. I | −6 ppm (multi) | 74 |
|  | −10 ppm (multi) | 21 |
|  | −20.5, −22.0 ppm | 5 |
| Ex. II | −5, −7 ppm (multi) | 71 |
|  | −10 ppm (multi) | 22 |
|  | −19.6, −20.9 ppm | 7 |
| Ex. III | −7.1 ppm | 92 |
|  | +17 ppm | 8 |
| Ex. IV | +8 ppm (multi) | 45 |
|  | +18 ppm (multi) | 44 |
|  | −19.5, −22.1 ppm | 11 |
| Ex. V | +6 ppm (multi) | 44 |
|  | +16 ppm (multi) | 40 |
|  | −20, −21.8 ppm | 16 |
| Ex. VI | −15 ppm (multi) | 77 |
|  | +16 ppm | 5 |
|  | −22.1, −24 ppm | 18 |
| Ex. VII | −4, −6 ppm (multi) | 61 |
|  | −10 ppm (multi) | 28 |
|  | −19.5, −21 ppm | 11 |
| Et$_2$SiH | +0.3 ppm | 100 |
| Et$_2$SiH$_2$ | −22.8 ppm | 100 |
| HexSiH$_3$ | −59.6 ppm | 100 |
| Ph$_2$SiH$_2$ | −33.2 ppm | 100 |

In Table II above, the top entry for each of the experimental reaction products Si$^{29}$ NMR peaks is the area assigned to the polyepoxysilane reaction product. Based solely on the NMR data, epoxysilane formation proceeded most smoothly in the case of the Et$_3$SiH adduct with VCHO. The extraneous peak in this case is attributed to Et$_3$Si(OEt)+Et$_3$SiOSi(Et)$_2$E "M"-containing monomers. Other reaction products were more complex, including significant amounts of polysiloxanes (indicated by NMR peaks at about 20 ppm), such as, for example, M$^E$DM$^E$ and M$^E$D$_x$M$^{E2}$. Polyepoxysilane yields ranged from about 77% for the hexylsilane derivative to slightly less than 50% for the diethylsilane derivatives. While these results are less than ideal, the complex reaction products are not surprising in view of the presence of ethanol, introduced with the RhCl$_3$.xH$_2$O catalyst. No effort was made to rigorously dry the reaction solvents because such a procedure is normally not compatible with routine manufacturing practices. Elemental analyses of these reaction products were not conclusive; in each case, less carbon and greater amounts of Si than theoretical percentages were found, supporting NMR based conclusions that siloxanes were present in the products.

Regardless of the purity of the experimental reaction products, UV cure activity of these compositions is good. All products proved miscible with 1 weight percent (4-octyloxyphenyl) phenyl iodoniumhexafluoroantimonate photocatalyst. 2 mil coatings applied to the polyethylene-kraft substrate were exposed to UV light and the minimum UV flux required for cure to tack- and migration-free coatings was ascertained. UV-cure assessment results for all experimental compositions are tabulated below:

| Example # | Minimum UV Flux For Cure* |
|---|---|
| I | 25 mJ/cm$^2$ |
| II | 206 |
| III | (monomer: tacky film noted after exposure to 2000 mJ/cm$^2$) |
| IV | 17 |
| V | 190 |
| VI | 56 |
| VII | 184 |

*RPC medium pressure mercury vapor lamp

These cure results indicate that fastest cure is obtained for compositions where the epoxy groups are derived from VCHO which is similar to organic and silicone systems. Also, the less bulky ethyl groups in the diethylsilane derivatives promote faster cure under these conditions than hexyl-group or phenyl-group containing diepoxysilanes.

Compositions obtained from reaction of two moles of olefinepoxide with poly(H)silanes may be efficiently photocrosslinked to tack- and migration-free protective coatings when exposed to ultraviolet light in the presence of a catalytic amount of a compatible iodonium photocatalyst. The mono-functional epoxytriethylsilane behaves like other mono-cyclohexylepoxide monomers such as 4-vinylcyclohexeneoxide. Example III, mono-epoxytriethylsilane, although slow-curing by itself, is freely miscible with a diepoxymonomer sold by Ciba-Geigy as CY-179, and acts as a good reactive diluent for this material. 10 weight percent of Example III dispersed in CY-179 reduces coating viscosity from 400 to 200 cstk, and surprisingly speeds the UV cure response (2 mil film, 1% iodonium salt as before) from 300 mJ/cm$^2$ UV flux required to 180 mJ/cm$^2$. This is unexpected behavior, since monofunctional diluents normally slow the cure response of a UV-cure coating system.

While there have been described what at present are considered to be the preferred embodiments of the present invention, it will be readily apparent to those skilled in the art that various changes may be made herein without departing from the invention and it is intended in the claims to cover such changes and modifications as fall within the true spirit and scope of the invention.

What is claimed:

1. A polyepoxy silane of the general formula:

wherein $x > 1$ and wherein each E is independently selected from the group of epoxides of the general formula:

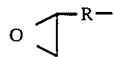

and each R is independently selected from the group consisting of a hydrocarbon having between 1 and about 20 carbon atoms, said polyepoxy silane produced from the hydrosilation reaction of epoxide monomers and a silane in the presence of a catalytic amount of a rhodium catalyst.

2. The polyepoxysilane according to claim 1, wherein E is selected from the group of epoxide monomers consisting of:

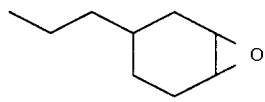

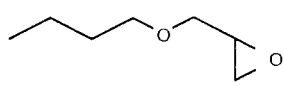

and

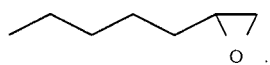

3. The polyepoxysilane according to claim 1, wherein E represents the radical

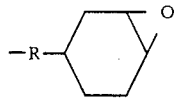

wherein each R is an alkylene radical having from 1 to about 8 carbon atoms.

4. The polyepoxysilane according to claim 3, wherein R is an ethylene radical.

5. The polyepoxysilane according to claim 1, wherein E is a radical of vinylcyclohexeneoxide.

6. The polyepoxysilane according to claim 1, wherein E is a radical of propylglycidylether.

7. The polyepoxysilane according to claim 1, wherein E is a radical of -5,6-epoxyhexane.

8. A polyepoxysilyl-stopped siloxane composition having the general formula:

where
X = 2 or 3
R and R' are hydrocarbons having from 1 to about 20 carbon atoms and y is an integer up to about 100.

9. The polyepoxysilane according to claim 8, wherein y ranges from about 25 to about 75.

10. The polyepoxysilane according to claim 8, wherein R is the radical —CH$_3$.

11. The composition according to claim 8, wherein R' is the radical —CH$_2$CH$_2$—.

12. The composition according to claim 8, wherein the silane is produced from the hydrosilation reaction of epoxide monomers and a silane in the presence of a catalytic amount of rhodium catalyst.

13. A composition according to claim 8, having the general formula

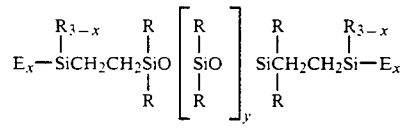

where x is 2 or 3, and y > about 50.

14. A composition according to claim 13, wherein E is a radical of vinylcyclohexeneoxide.

15. A composition according to claim 13, wherein E is a radical of alkylglycidylether.

16. A composition according to claim 13, wherein R is an alkene radical having from 1 to about 8 carbon atoms.

17. A composition according to claim 16, wherein R is an ethylene radical.

18. UV curable polyepoxysilanes comprising:
compositions obtained from reaction of up to 2 moles of olefinepoxide and poly(H)silanes in the presence of a rhodium catalyst, plus compatible 'onium-type cationic photocatalysts.

* * * * *